(12) United States Patent
Woodward (10) Patent No.: US 12,220,247 B2
(45) Date of Patent: *Feb. 11, 2025

(54) PORTABLE POLYSOMNOGRAPHY APPARATUS AND SYSTEM

(71) Applicant: United States Government as Represented by the Department of Veterans Affairs, Washington, DC (US)

(72) Inventor: Steven Hartwell Woodward, Palo Alto, CA (US)

(73) Assignee: United States Government As Represented By The Department Of Veterans Affairs, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/472,497

(22) Filed: Sep. 22, 2023

(65) Prior Publication Data

US 2024/0008808 A1    Jan. 11, 2024

Related U.S. Application Data

(63) Continuation of application No. 17/100,163, filed on Nov. 20, 2020, now Pat. No. 11,779,266, which is a continuation of application No. 13/912,405, filed on Jun. 7, 2013, now Pat. No. 10,856,800.

(60) Provisional application No. 61/657,190, filed on Jun. 8, 2012.

(51) Int. Cl.
*A61B 5/00* (2006.01)
*A61B 5/11* (2006.01)
*A61B 5/145* (2006.01)

(52) U.S. Cl.
CPC .......... *A61B 5/4806* (2013.01); *A61B 5/0002* (2013.01); *A61B 5/002* (2013.01); *A61B 5/14542* (2013.01); *A61B 5/6887* (2013.01); *A61B 5/6892* (2013.01); *A61B 5/11* (2013.01); *A61B 5/70* (2013.01); *A61B 2562/0219* (2013.01)

(58) Field of Classification Search
CPC ..... A61B 5/4806; A61B 5/0002; A61B 5/002; A61B 5/14542; A61B 5/6887; A61B 5/6892; A61B 5/11; A61B 5/70; A61B 2562/0219
USPC ......................................................... 600/301
See application file for complete search history.

(56) References Cited

U.S. PATENT DOCUMENTS

| | | | | |
|---|---|---|---|---|
| 2007/0118054 A1* | 5/2007 | Pinhas | .................... | G16H 40/67 600/587 |
| 2008/0009685 A1* | 1/2008 | Kim | ........................ | A61B 5/33 600/300 |
| 2013/0276785 A1* | 10/2013 | Melker | ............. | A61M 16/0677 128/204.23 |

* cited by examiner

*Primary Examiner* — Joseph M Dietrich
*Assistant Examiner* — Michael T. Holtzclaw
(74) *Attorney, Agent, or Firm* — Ballard Spahr LLP

(57) ABSTRACT

A portable polysomnography apparatus comprises a unitary flexible structured pillow that is embedded with one or more sensors for data collection. The one or more sensors can comprise a tilt sensor that is configured to generate respiratory effort signals based on tilting of the head of the subject on the pillow. The one or more sensors can further be configured to generate ballistocardiogram signals from movement of the head of the subject caused by beating of the heart of the subject. The polysomnography apparatus can be advantageously sized and shaped to cause the sleeping subject to properly orient her head with respect to the sensors for optimal data collection while the subject is asleep.

20 Claims, 7 Drawing Sheets

PORTABLE POLYSOMNOGRAPHY APPARATUS AND SYSTEM

CROSS-REFERENCE TO RELATED APPLICATIONS

This application is a continuation of U.S. patent application Ser. No. 17/100,163, filed Nov. 20, 2020, which is a continuation of U.S. patent application Ser. No. 13/912,405, filed Jun. 7, 2013, which claims priority to and the benefit of the filing date of U.S. Provisional Application No. 61/657,190, filed Jun. 8, 2012. Each of the foregoing applications is hereby incorporated by reference herein in its entirety.

FIELD OF THE INVENTION

The present invention is generally related to polysomnography and is more specifically related to zero burden sleep recording in laboratory polysomnography or ambulatory (i.e., at home) polysomnography.

RELATED ART

Conventional sleep recording or polysomnography is typically performed in a sleep laboratory using a plurality of body-surface sensors (electrodes, elastic bands, etc.) to record various medically significant features of sleep such as electrocardiogram and respiratory movements or efforts at thorax and abdomen. The attachment of sensors using glue and tape and the routing of wires along the skin typically requires ninety minutes or more and is performed by a trained polysomnographic technician. Consequently, the pre-sleep period is substantially modified and the subsequent sleeping conditions are widely acknowledged to be aberrant. Ambulatory versions of polysomnography using portable battery-powered recorders allow conventional sleep recording to be performed at a subject's home, however the same amount of technician time is required, the same discomforts associated with the body-surface sensors are present and therefore the pre-sleep period is still substantially modified resulting in questionable data collection.

In conventional polysomnography, there are several levels of sleep recording: (1) high burden polysomnography that takes place in the laboratory and is the most intrusive but yields the highest level of data collection for analysis; (2) medium burden polysomnography typically takes place in the subject's home and is slightly less intrusive but only allows for level three screening, which results in limited data collection for analysis; and (3) low burden polysomnography such as a wrist actigraph that is substantially less intrusive but only collects a small amount of information for analysis.

Accordingly, conventional polysomnography suffers from the natural tension between the necessary intrusion on the subject to record the features of sleep and the related disruption of natural sleep that results from this intrusion. Consequently, conventional polysomnography has been attempting to solve the problem of how to collect rich data without interrupting the sleep patterns of the subject. One solution described in U.S. Pat. No. 6,485,441 (which is incorporated by reference herein in its entirety) is to remove the sensors from the skin of the subject and put the sensors into a mattress upon which the subject sleeps. While this clearly lowers the intrusion on the subject's sleep patterns, it reduces the fidelity of the data that is collected because cardiac data is collected along with respiratory data, making the resulting data sets very difficult to decipher. Therefore, there may be a need for a system or method that may address one or more of these problems.

SUMMARY

One or more embodiments consistent with the present application may address some of the issues discussed above.

An embodiment of the present application may include a portable polysomnography apparatus comprising a unitary flexible structured pillow that is embedded with one or more sensors for data collection. Further, an embodiment may be sized and shaped to cause the sleeping subject to orient the embedded sensors for optimal data collection while the subject is asleep. Additionally, an embodiment may be formed as a structured pillow to focus the data collection on the subject's head.

According to one aspect of the present application, a polysomnography system may include a structured pillow with embedded sensors that are in communication with a companion data collection device that records data from the embedded sensors. According to another aspect of the present application, a system may include a structured pillow with an internal pocket into which a single device including embedded sensors and data recording capabilities is inserted. In some embodiments, an existing device owned by the subject may be modified with a special purpose computer program and/or hardware device to allow for efficient and low cost ambulatory polysomnography in the subject's home.

Other features of the present application may become more readily apparent to those of ordinary skill in the art after reviewing the following detailed description and accompanying drawings.

BRIEF DESCRIPTION OF THE DRAWINGS

The structure and operation of the present invention will be understood from a review of the following detailed description and the accompanying drawings in which like reference numerals refer to like parts and in which.

DETAILED DESCRIPTION

Certain embodiments disclosed herein provide for a polysomnography apparatus that comprises a structured pillow with one or more embedded sensors that are communicatively coupled with an integrated or remote data collection device. After reading this description it will become apparent to one skilled in the art how to implement the present application in various alternative embodiments and alternative uses. However, although various embodiments of the present application may be described herein, it is understood that these embodiments are presented by way of example only, and not limitation. As such, this detailed description of various embodiments should not be construed to limit the scope or breadth of the present invention as set forth in the appended claims.

Figure 1:
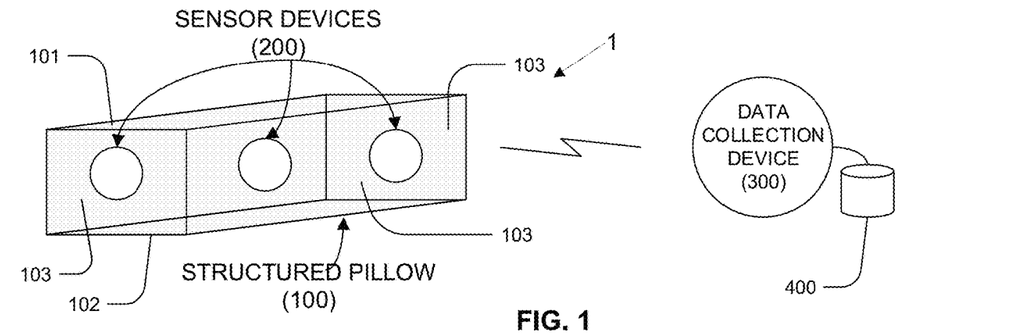
FIG. 1 is a block diagram illustrating an example polysomnography system according to a first embodiment of the invention.

FIG. 1 is a block diagram illustrating an example polysomnography system according to an embodiment of the invention. In the illustrated embodiment of FIG. 1, the system comprises a structured pillow 100 having one or more sensor devices 200. The sensor devices 200 may be communicatively coupled with a data collection device 300 that has an associated data storage area 400. In other embodiments, the one or more sensor devices 200 may themselves include an associated data storage area. The one or more sensor devices 200 take measurements and readings that are related to a subject who is using the polysomnography system and communicates those measurements and readings to the data collection device. In other words, the one or more sensor devices 200 take measurements and readings of a subject using the structured pillow 100. In some embodiments, the measurements and readings may also be stored on the one or more sensor devices 200 themselves prior to or after communication of the measurements and readings to the data collection device 300. The communication of the measurements and readings may take place wirelessly, for example via a wireless communication network, a Bluetooth® link, an infrared link or other wireless communication link. The communication of the measurements and readings may also be performed via wired communication. The sensor devices and the data collection device can be any sort of processor enabled device such as later described with respect to FIG. 4.

The structured pillow 100 may comprise a unitary flexible material such as a foam or another material that regains its shape after compression. In one embodiment, the structured pillow 100 may alternatively comprise a layered ply of material that is also unitary and flexible despite having a composite construction. In one embodiment the structured pillow 100 has a top 101, bottom 102 and a plurality of sides 103. The structured pillow 100 may be small and may naturally focus on the head of the subject during sleep.

In one embodiment, the one or more sensors 200 can be optimally oriented inside the flexible material of the structured pillow 100 in order to sense ballistocardiogram signals from the heart of the subject and to additionally sense respiratory effort signals from the breathing of the subject. Specifically, the longitudinal coupling of the head of the subject to the thorax of the subject causes the head to be a reliable source of the ballistocardiogram signal. This may allow robust sensing of the ballistocardiogram signal in a pillow device that is naturally focused on the head of the subject during sleep. Additionally, although the head does not expand and contract as the subject breathes (e.g., in part because the skull is thick and inflexible), the movement of the thorax as the subject breathes causes the head to tilt on the structured pillow 100 and thereby the sensors 200 in the structured pillow 100 may sense respiratory effect signals by sensing the movement of the subject's head on the structured pillow 100.

In one embodiment, the structured pillow 100 may be augmented with an uncomfortable material on the surface or disposed adjacent to the surface to cause the sleeping subject to orient the structured pillow in a desired fashion that optimizes the location of the sensors 200 to the head of the sleeping subject. Examples of uncomfortable material may include any material that causes the subject to attempt to avoid the material such as a rough fabric, a rigid plastic or metallic portion, or any other material that provides a haptic cue causing the subject to adjust the placement of pillow that may be apparent to a person of ordinary skill in the art. Other alternatives for encouraging the sleeping subject to orient the structured pillow 100 in a desired way may also be employed, for example the shape of the pillow 100 can be designed with this purpose in mind.

In some embodiments, a single sensor 200 may be located in the center of the structured pillow 100 in order to normalize the sensing of the signal during sleep regardless of the orientation of the structured pillow 100. In some embodiments, the vertical placement of one or more of the sensors 200 may be biased to be positioned closer to the subject's head than the mattress. In some embodiments, the one or more sensors 200 in the structured pillow may be three dimensional/tri-axial accelerometers. However, alternative types of sensors 200 may be selected to measure the subject's head movement with respect to the structured pillow 100 as would be apparent to a person of ordinary skill in the art.

The small portable nature of the structured pillow 100 may allow the pillow 100 to be used in a variety of applications and particularly for ambulatory polysomnography. For example, a patient may take the structured pillow 100 and data collection device 300 home and use the pillow 100 overnight and then return the pillow 100 and data collection device 300 to the doctor for analysis. In some embodiments, the data collection device 300 and sensors 200 may be sealed inside the structured pillow for security and simplicity. In an alternative embodiment, the data collection device 300 may be an application that is downloaded onto a wireless communication device (e.g., a smartphone) of the subject and configured to communicate with the sensors 200 in the pillow. The application may then send the data to the doctor for analysis via a data communication network (e.g., cellular communications network).

Figure 3A:
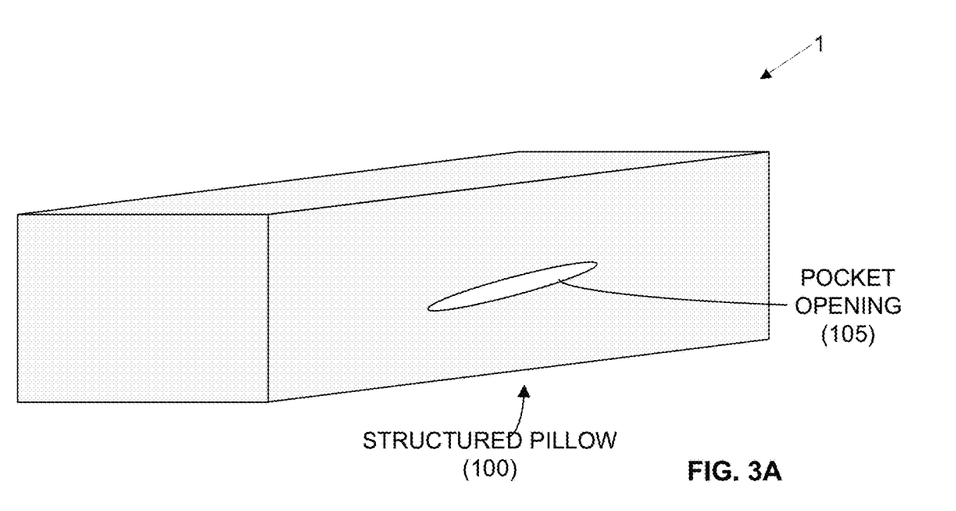
FIGS. 3A and 3B are block diagrams illustrating an example polysomnography apparatus with an internal pocket having a pocket opening on the surface of the polysomnography apparatus according to a second embodiment of the invention.
Figure 3B:
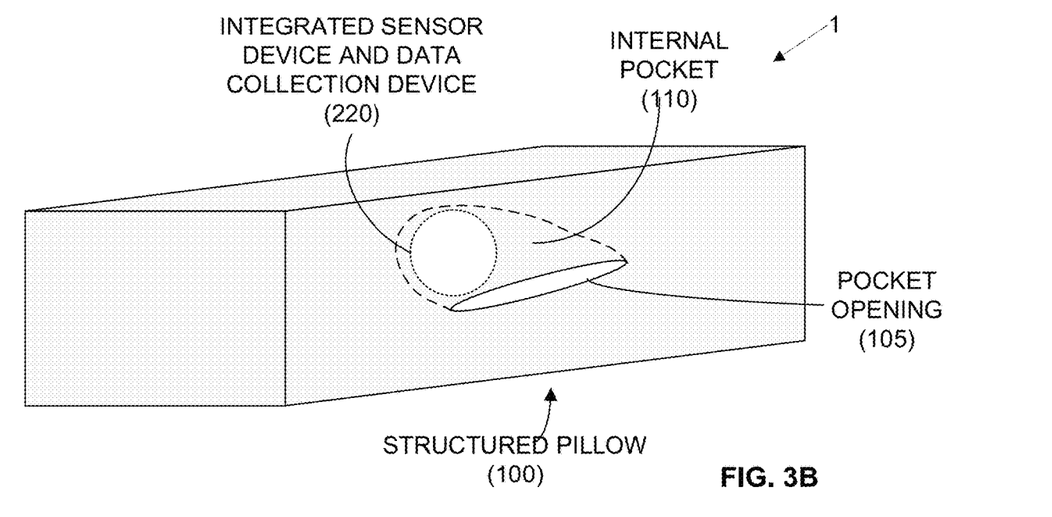

In some embodiments, a sensor device 200 may be provided to the subject and then connected to a wireless communication device 300 of the subject and inserted into the structured pillow 100 through a pocket opening 105 formed in one or more of the top 101, bottom 102, or sides 103 (shown in FIGS. 3A and 3B). The sensor device 220 in such an embodiment may include both the sensors 200 as well as the data collection device 300 (shown in FIG. 3B). The sensor device 220 may then be returned to the doctor for analysis of the collected data.

Figure 2A:
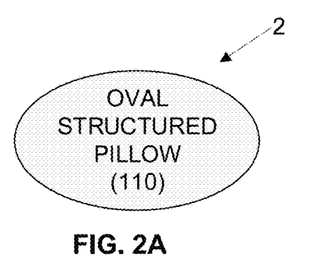
FIGS. 2A-2C are block diagrams illustrating example alternative shapes for a polysomnography apparatus according to an embodiment of the invention.
Figure 2B:
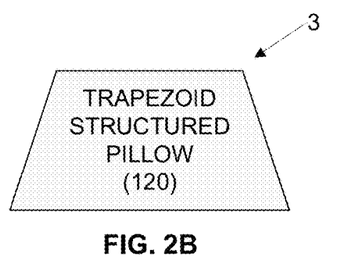
Figure 2C:
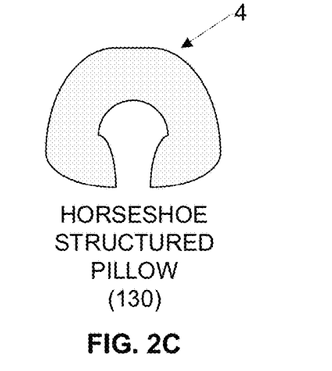

FIGS. 2A-2C illustrate example alternative shapes for a polysomnography apparatus 2, 3, 4 according to an embodiment of the invention. In the illustrated embodiments, the polysomnography apparatus 2 includes a structured pillow 110 having an oval shape in FIG. 2A, the polysomnography apparatus 3 includes a structured pillow 120 having a trapezoidal shape in FIG. 2B and the polysomnography apparatus 4 includes a structured pillow 130 having a horseshoe shape in FIG. 2C. As will be understood by those skilled in the art, alternative shapes may also be employed to affect the subject's orientation of the pillow while sleeping in order to optimize the positioning of the sensor devices with respect to the head of the subject.

FIGS. 3A and 3B illustrate an example polysomnography apparatus 1 with an internal pocket 110 having a pocket opening 105 on the surface of the polysomnography apparatus 1 and including an integrated sensor device and data collection device 220 positioned in the internal pocket according to an embodiment of the invention.

In the illustrated embodiment, a portable sensor device 220 may be inserted into the pocket 110 of the structured pillow 100. The data collection device may be integrated with the sensor device in such an embodiment. In other embodiments, there may be a plurality of pockets in the structured pillow so that one or more sensor devices can be inserted into the pockets, depending on the desired data collection. These sensors can be dynamically configured to communicate, wirelessly or through a wired connection, with a remote data collection device that is placed near the pillow. The data collection device may alternatively be placed inside an additional pocket of the structured pillow.

In the above discussed embodiments, the sensors 200 are disposed within (i.e., in the interior of) the pillow 100. However, in some embodiments, the sensors 200 may be formed to have a thin-profile and may be positioned near the surface of the pillow 100 or may be adhered to the exterior surface of the pillow 100. In some embodiments, the sensors 200 may be disposed between the exterior surface of the pillow 100 and a pillow case (not labeled). In other embodiments, the sensors 200 may be attached to the outside of the pillow case.

Figure 4A:
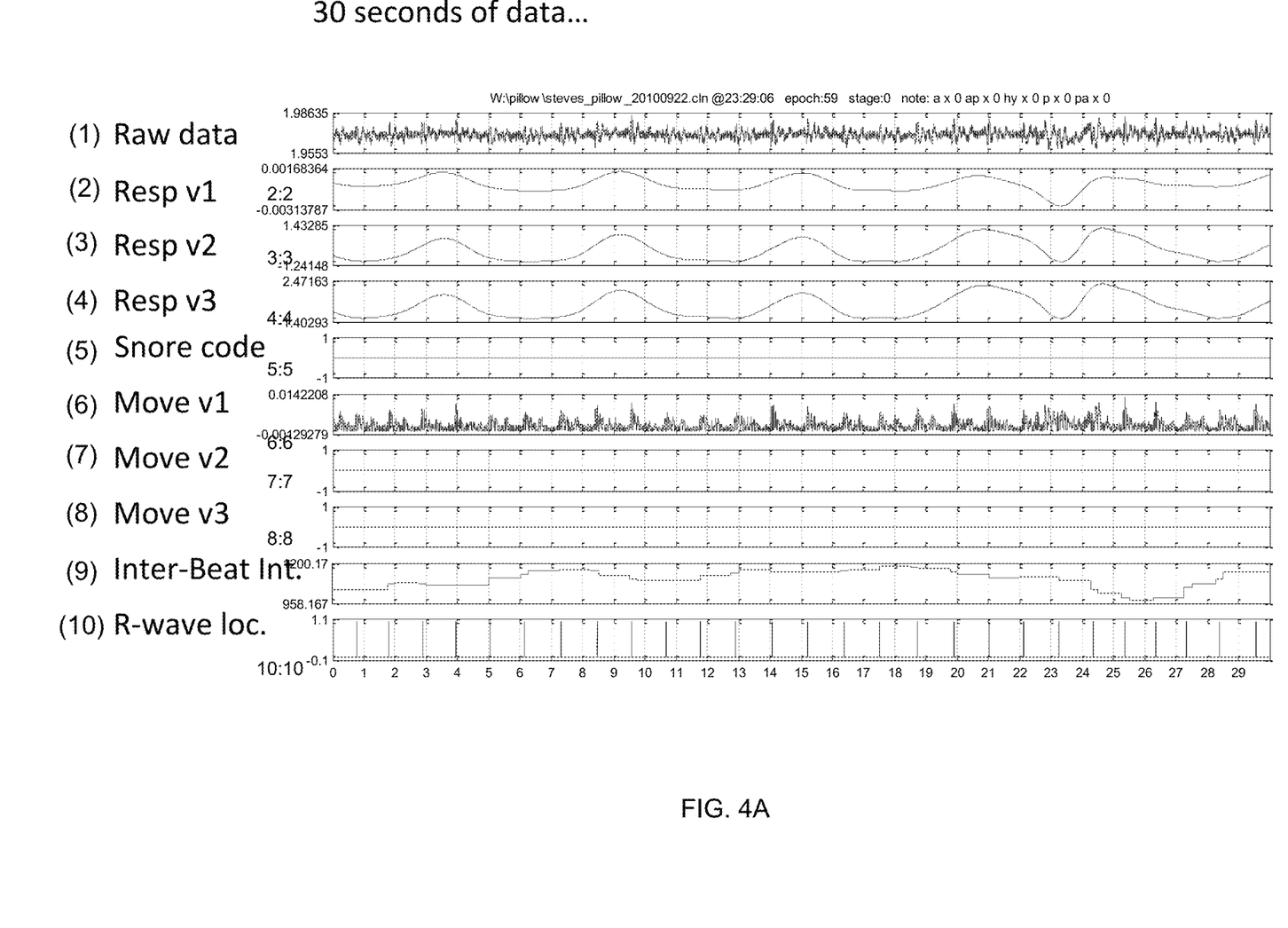
FIGS. 4A-4E are graph diagrams illustrating example polysomnography data sets collected by an apparatus according to an embodiment of the invention.
Figure 4B:
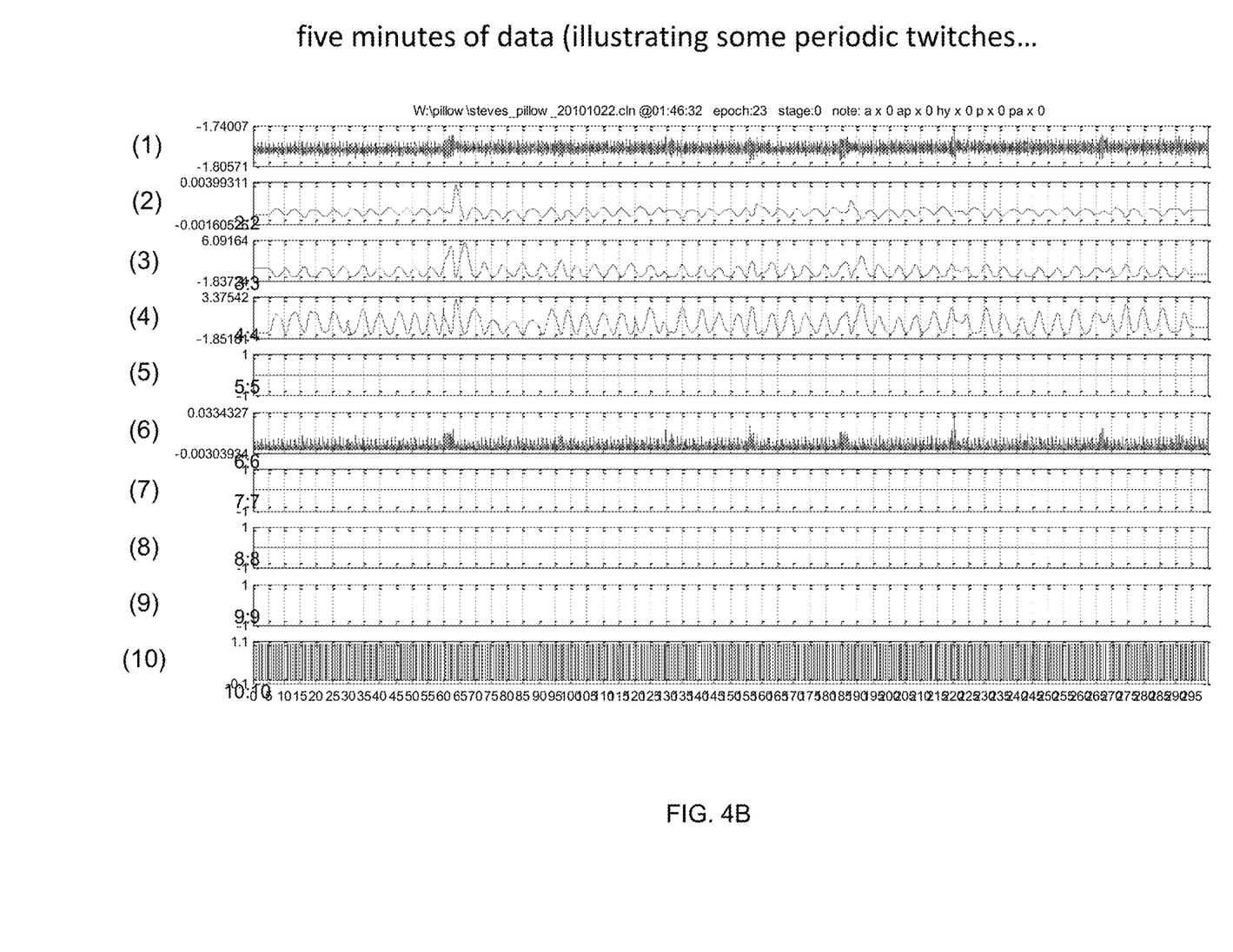

FIGS. 4A-4E are graph diagrams illustrating example polysomnography data sets that may be collected by an apparatus according to an embodiment of the invention. FIGS. 4A and 4B illustrate data collected at different sample rates over different time intervals (30 seconds (FIGS. 4A) and 5 minutes (FIG. 4B). Strips (1) illustrate raw sensor pillow data. Strips (2)-(4) illustrate versions of respiratory movement data from Strip (1) after application of strict band-pass filtering. Further, strip (5) represents snoring measured during the measured epoch and strips (6)-(8) represented sensed body movement during the measured epoch. It should be noted that strips (3) and (4) have similar appearances over this epoch because there no sensible body movement. This also explains why there are no movement codings in Strips 7 & 8. Further, Strip 9 illustrates inter-beat-intervals, and Strip 10 indexes R-wave locations during the Epoch. As shown by these FIGURES, using the sensor pillow allows sampling with greater sensitivity compared to wrist actigraphy sensors allowing sampling at higher sample rates (20 htz or greater for the pillow sensor compared once or twice per minute for wrist actigraphy).

Figure 4C:
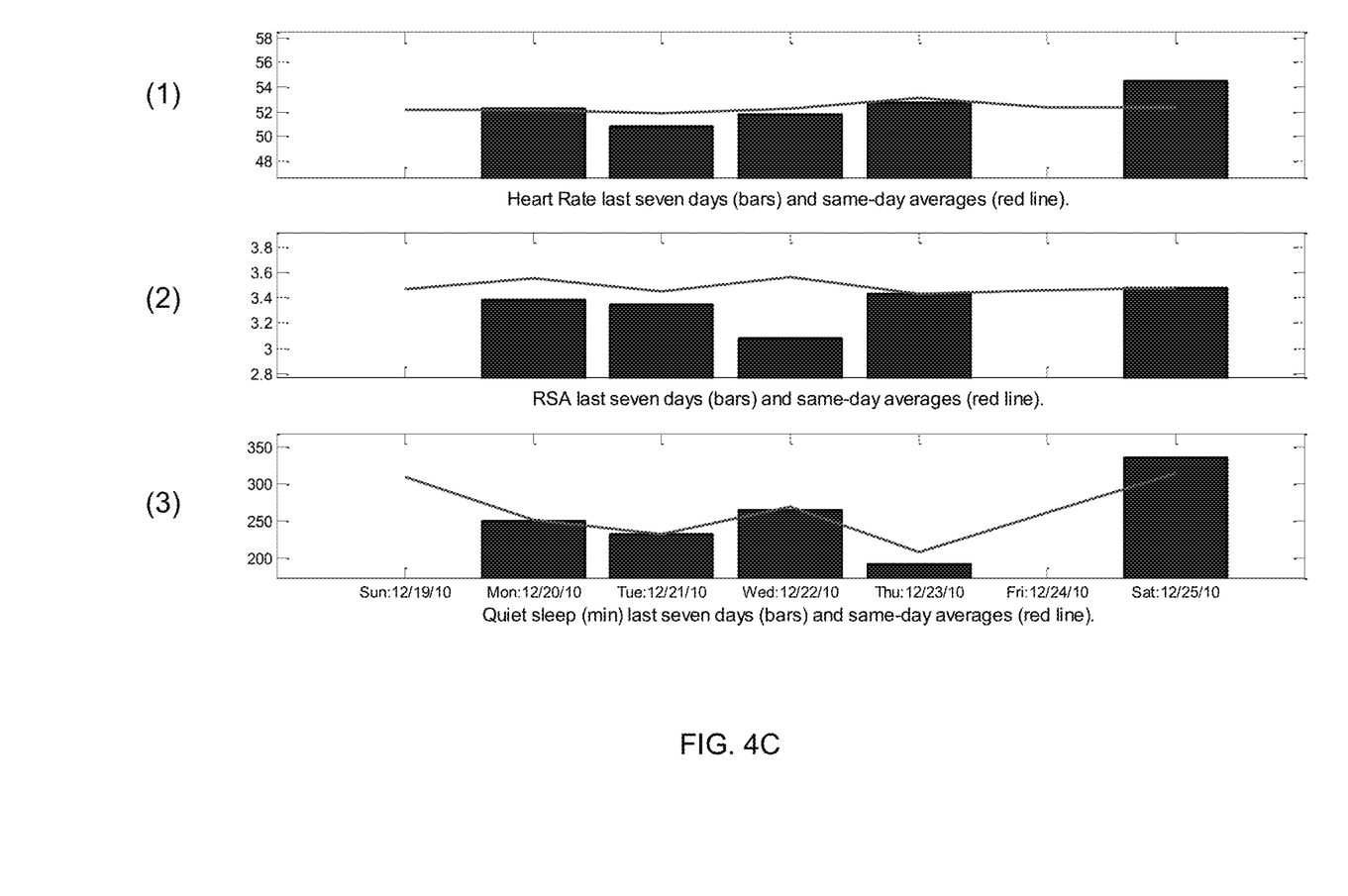
Figure 4D:
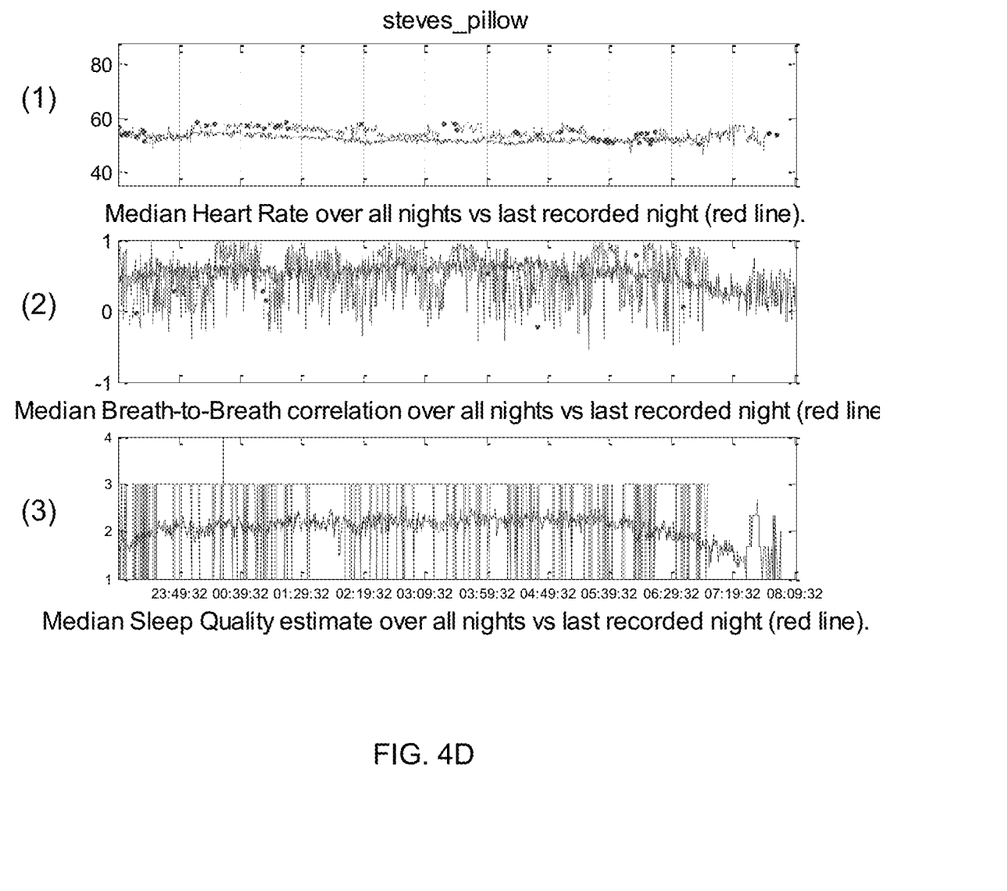

Further, FIGS. 4C and 4D illustrate data collected over multiple nights compared to a most recent night. Specifically, FIG. 4C illustrates comparisons between averages over a seven day period (Bars) and averages for a single day. In FIG. 4C, strip (1) represents heart rate, strip (2) represents Respiratory sinus arrhythmia (RSA), and strip (3) represents quiet sleep time in minutes. Additionally, FIG. 4D illustrates comparisons between average data over all nights and a most recent night. In FIG. 4D, strip (1) represents heart rate, strip (2) represents breath to breath correlations, and strip (3) represents median sleep quality. These visualization paradigms are merely examples and other visualization paradigms may be used to visualize data collected using example embodiments of the present application.

Figure 4E:
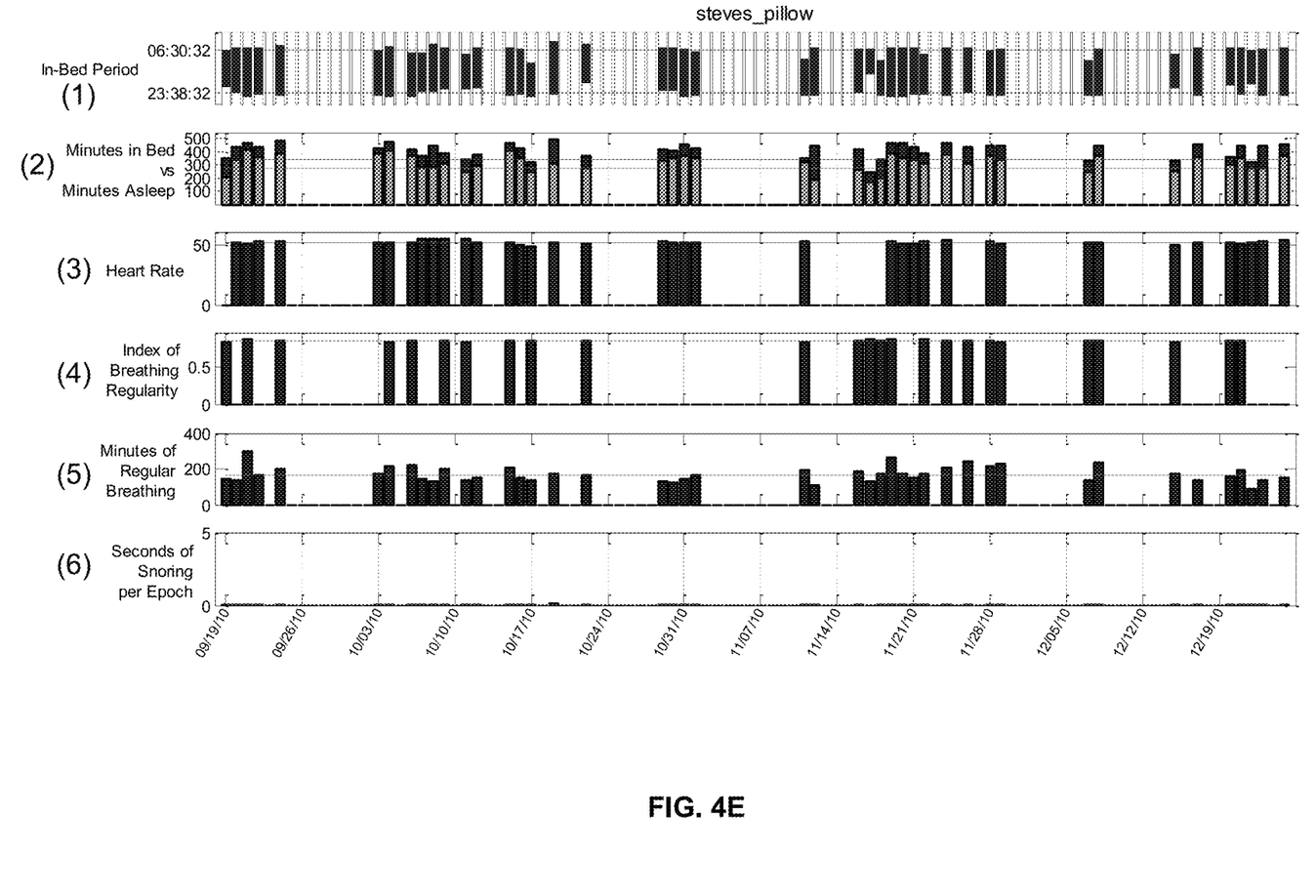

Further, FIG. 4E illustrates data recorded over a three month period. In FIG. 4E, Strip (1) is the sleep period according to clock times and strip (2) is minutes in bed and in presumed sleep. Further, strip (3) is mean all-night heart rate and strip (4) is a measure of breathing regularity relevant to sleep-disordered breathing. Further, strip 5 is a measure of very quiet sleep as indexed by respiration and strip 6 is seconds of snoring per epoch. These are all indices that may be extracted from sensor pillow data that are not available from conventional wrist actigraphy. Additionally, these indices illustrate the principal that low-burden (or zero burden) imposed on a subject using a sensor pillow (as compared to other polysomnography systems) may allow for very long extended periods of time and potentially, even indefinitely. It should be noted that gaps shown in the data of FIG. 4E represent nights when the subject was unavailable to use the sensor pillow due to travel, or, in a few cases, data excluded due to the imposition of strict quality criteria.

Figure 5:
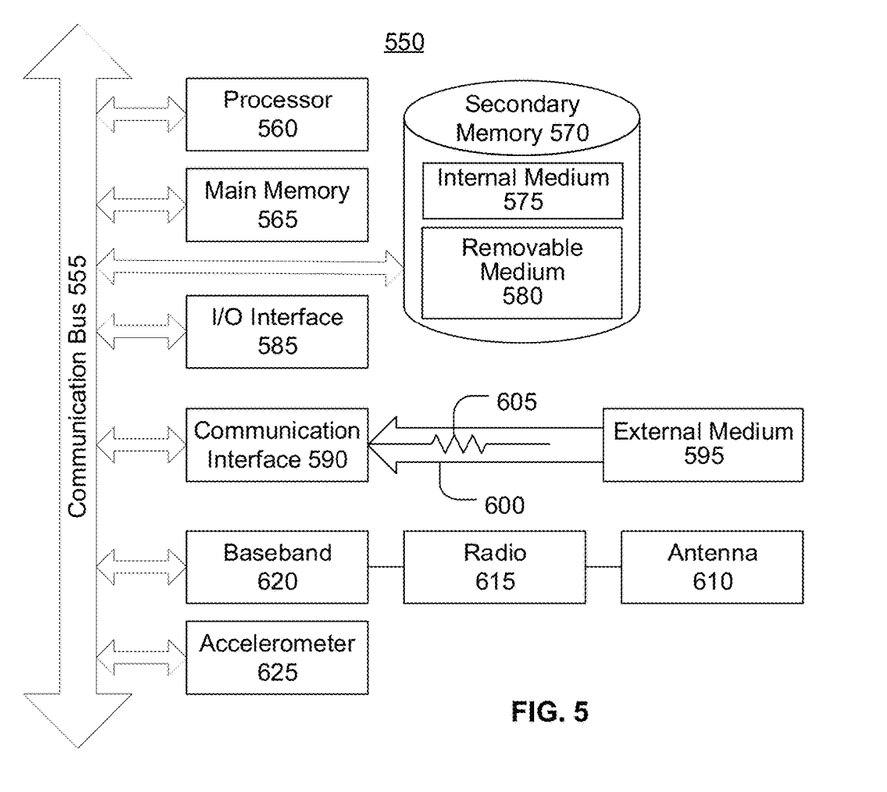
FIG. 5 is a block diagram illustrating an example wired or wireless processor enabled device that may be used in connection with one or more embodiments described herein.

FIG. 5 is a block diagram illustrating an example wired or wireless system 550 that may be used in connection with various embodiments described herein. For example the system 550 may be used as or in conjunction with a sensor device or a data collection device as previously described with respect to FIGS. 1 and 3A-3B. The system 550 can be a conventional personal computer, computer server, personal digital assistant, smart phone, tablet computer, or any other processor enabled device that is capable of wired or wireless data communication. Other computer systems and/or architectures may be also used, as will be clear to those skilled in the art.

The system 550 preferably includes one or more processors, such as processor 560. Additional processors may be provided, such as an auxiliary processor to manage input/output, an auxiliary processor to perform floating point mathematical operations, a special-purpose microprocessor having an architecture suitable for fast execution of signal processing algorithms (e.g., digital signal processor), a slave processor subordinate to the main processing system (e.g., back-end processor), an additional microprocessor or controller for dual or multiple processor systems, or a coprocessor. Such auxiliary processors may be discrete processors or may be integrated with the processor 560.

The processor 560 is preferably connected to a communication bus 555. The communication bus 555 may include a data channel for facilitating information transfer between storage and other peripheral components of the system 550. The communication bus 555 further may provide a set of signals used for communication with the processor 560, including a data bus, address bus, and control bus (not shown). The communication bus 555 may comprise any standard or non-standard bus architecture such as, for example, bus architectures compliant with industry standard architecture ("ISA"), extended industry standard architecture ("EISA"), Micro Channel Architecture ("MCA"), peripheral component interconnect ("PCI") local bus, or standards promulgated by the Institute of Electrical and Electronics Engineers ("IEEE") including IEEE 488 general-purpose interface bus ("GPIB"), IEEE 696/S-100, and the like.

System 550 preferably includes a main memory 565 and may also include a secondary memory 570. The main memory 565 provides storage of instructions and data for programs executing on the processor 560. The main memory 565 is typically semiconductor-based memory such as dynamic random access memory ("DRAM") and/or static random access memory ("SRAM"). Other semiconductor-based memory types include, for example, synchronous dynamic random access memory ("SDRAM"), Rambus dynamic random access memory ("RDRAM"), ferroelectric random access memory ("FRAM"), and the like, including read only memory ("ROM").

The secondary memory 570 may optionally include a internal memory 575 and/or a removable medium 580, for example a floppy disk drive, a magnetic tape drive, a compact disc ("CD") drive, a digital versatile disc ("DVD") drive, etc. The removable medium 580 is read from and/or written to in a well-known manner. Removable storage medium 580 may be, for example, a floppy disk, magnetic tape, CD, DVD, SD card, etc.

The removable storage medium 580 is a non-transitory computer readable medium having stored thereon computer executable code (i.e., software) and/or data. The computer software or data stored on the removable storage medium 580 is read into the system 550 for execution by the processor 560.

In alternative embodiments, secondary memory 570 may include other similar means for allowing computer programs or other data or instructions to be loaded into the system 550. Such means may include, for example, an external storage medium 595 and an interface 570. Examples of external storage medium 595 may include an external hard disk drive or an external optical drive, or and external magneto-optical drive.

Other examples of secondary memory 570 may include semiconductor-based memory such as programmable read-only memory ("PROM"), erasable programmable read-only memory ("EPROM"), electrically erasable read-only memory ("EEPROM"), or flash memory (block oriented memory similar to EEPROM). Also included are any other removable storage media 580 and communication interface 590, which allow software and data to be transferred from an external medium 595 to the system 550.

System 550 may also include a communication interface 590. The communication interface 590 allows software and data to be transferred between system 550 and external devices (e.g. printers), networks, or information sources. For example, computer software or executable code may be transferred to system 550 from a network server via communication interface 590. Examples of communication interface 590 include a modem, a network interface card ("NIC"), a wireless data card, a communications port, a PCMCIA slot and card, an infrared interface, and an IEEE 1394 fire-wire, just to name a few.

Communication interface 590 preferably implements industry promulgated protocol standards, such as Ethernet IEEE 802 standards, Fiber Channel, digital subscriber line ("DSL"), asynchronous digital subscriber line ("ADSL"), frame relay, asynchronous transfer mode ("ATM"), integrated digital services network ("ISDN"), personal communications services ("PCS"), transmission control protocol/Internet protocol ("TCP/IP"), serial line Internet protocol/point to point protocol ("SLIP/PPP"), and so on, but may also implement customized or non-standard interface protocols as well.

Software and data transferred via communication interface 590 are generally in the form of electrical communication signals 605. These signals 605 are preferably provided to communication interface 590 via a communication channel 600. In one embodiment, the communication channel 600 may be a wired or wireless network, or any variety of other communication links. Communication channel 600 carries signals 605 and can be implemented using a variety of wired or wireless communication means including wire or cable, fiber optics, conventional phone line, cellular phone link, wireless data communication link, radio frequency ("RF") link, or infrared link, just to name a few.

Computer executable code (i.e., computer programs or software) is stored in the main memory 565 and/or the secondary memory 570. Computer programs can also be received via communication interface 590 and stored in the main memory 565 and/or the secondary memory 570. Such computer programs, when executed, enable the system 550 to perform the various functions of the present invention as previously described.

In this description, the term "computer readable medium" is used to refer to any non-transitory computer readable storage media used to provide computer executable code (e.g., software and computer programs) to the system 550. Examples of these media include main memory 565, secondary memory 570 (including internal memory 575, removable medium 580, and external storage medium 595), and any peripheral device communicatively coupled with communication interface 590 (including a network information server or other network device). These non-transitory computer readable mediums are means for providing executable code, programming instructions, and software to the system 550.

In an embodiment that is implemented using software, the software may be stored on a computer readable medium and loaded into the system 550 by way of removable medium 580, I/O interface 585, or communication interface 590. In such an embodiment, the software is loaded into the system 550 in the form of electrical communication signals 605. The software, when executed by the processor 560, preferably causes the processor 560 to perform the inventive features and functions previously described herein.

The system 550 also includes optional wireless communication components that facilitate wireless communication over a voice and over a data network. The wireless communication components comprise an antenna system 610, a radio system 615 and a baseband system 620. In the system 550, radio frequency ("RF") signals are transmitted and received over the air by the antenna system 610 under the management of the radio system 615.

In one embodiment, the antenna system 610 may comprise one or more antennae and one or more multiplexors (not shown) that perform a switching function to provide the antenna system 610 with transmit and receive signal paths. In the receive path, received RF signals can be coupled from a multiplexor to a low noise amplifier (not shown) that amplifies the received RF signal and sends the amplified signal to the radio system 615.

In alternative embodiments, the radio system 615 may comprise one or more radios that are configured to communicate over various frequencies. In one embodiment, the radio system 615 may combine a demodulator (not shown) and modulator (not shown) in one integrated circuit ("IC"). The demodulator and modulator can also be separate components. In the incoming path, the demodulator strips away the RF carrier signal leaving a baseband receive audio signal, which is sent from the radio system 615 to the baseband system 620.

If the received signal contains audio information, then baseband system 620 decodes the signal and converts it to an analog signal. Then the signal is amplified and sent to a speaker. The baseband system 620 also receives analog audio signals from a microphone. These analog audio signals are converted to digital signals and encoded by the baseband system 620. The baseband system 620 also codes the digital signals for transmission and generates a baseband transmit audio signal that is routed to the modulator portion of the radio system 615. The modulator mixes the baseband transmit audio signal with an RF carrier signal generating an RF transmit signal that is routed to the antenna system and may pass through a power amplifier (not shown). The power amplifier amplifies the RF transmit signal and routes it to the antenna system 610 where the signal is switched to the antenna port for transmission.

The baseband system 620 is also communicatively coupled with the processor 560. The central processing unit 560 has access to data storage areas 565 and 570. The central processing unit 560 is preferably configured to execute instructions (i.e., computer programs or software) that can be stored in the memory 565 or the secondary memory 570. Computer programs can also be received from the baseband processor 610 and stored in the data storage area 565 or in secondary memory 570, or executed upon receipt. Such computer programs, when executed, enable the system 550 to perform the various functions of the present invention as previously described. For example, data storage areas 565 and 570 may include various software modules (not shown) that were previously described.

The system 550 also includes sensor components that facilitate data collection from the sleeping subject. The sensor components comprise an accelerometer 620, a piezoelectric transducer capable of detecting movement on the pillow or any other type of sensor capable of detecting audio information, vibration, movement, pressure, force and other signals that are desirable in polysomnography analysis. Examples of other sensors may include electromyography sensors, electro-oculography sensors, nasal pressure sensors, electroencephalography sensors, pulse oximetry sensors, or any other sensor signals as would apparent to a person of ordinary skill in the art. As discussed above, the sensor components may be embedded in a structured pillow according various embodiments of the present application. Additional sensors may be provided outside of the pillow and communicating with the data collection device, as would be apparent to a person of ordinary skill in the art.

In the system 550, data collected by the accelerometer or other sensors 625 may be stored in main memory 565 or secondary memory 570 can also be provided to a remote device via the wireless communication components 610, 615 and 620 or the communication interface 590. Example sets of data collected by the accelerometer 625 were previously described with respect to FIGS. 4A-4E.

The accelerometer 625 is also communicatively coupled with the processor 560. The central processing unit 560 has access to data storage areas 565 and 570. The central processing unit 560 is preferably configured to execute instructions (i.e., computer programs or software) that can be stored in the memory 565 or the secondary memory 570 in order to implement the desired data collection by the accelerometer.

In one embodiment, one or more sensors and/or accelerometers may be integrated with a charging system (not shown) that attaches to a wireless communication device. The charging unit may advantageously recharge a battery in the wireless communication device while also comprising more sensitive sensors and/or accelerometers for use with the polysomnography system.

In one embodiment, the polysomnography system may include software modules that, upon determination that the subject is asleep (e.g., by detection of sleep onset/sleep pattern signals), are configured to wirelessly turn off "go-to-sleep" music being played by the polysomnography system or to wirelessly turn off a radio or television set that is in proximity of the subject.

Various embodiments may also be implemented primarily in hardware using, for example, components such as application specific integrated circuits ("ASICs"), or field programmable gate arrays ("FPGAs"). Implementation of a hardware state machine capable of performing the functions described herein will also be apparent to those skilled in the relevant art. Various embodiments may also be implemented using a combination of both hardware and software.

Furthermore, those of skill in the art will appreciate that the various illustrative logical blocks, modules, circuits, and method steps described in connection with the above described FIGURES and the embodiments disclosed herein can often be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled persons can implement the described functionality in varying ways for each particular application, but such implementation decisions should not be interpreted as causing a departure from the scope of the invention. In addition, the grouping of functions within a module, block, circuit or step is for ease of description. Specific functions or steps can be moved from one module, block or circuit to another without departing from the invention.

Moreover, the various illustrative logical blocks, modules, and methods described in connection with the embodiments disclosed herein can be implemented or performed with a general purpose processor, a digital signal processor ("DSP"), an ASIC, FPGA or other programmable logic device, discrete gate or transistor logic, discrete hardware components, or any combination thereof designed to perform the functions described herein. A general-purpose processor can be a microprocessor, but in the alternative, the processor can be any processor, controller, microcontroller, or state machine. A processor can also be implemented as a combination of computing devices, for example, a combination of a DSP and a microprocessor, a plurality of microprocessors, one or more microprocessors in conjunction with a DSP core, or any other such configuration.

Additionally, the steps of a method or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of storage medium including a network storage medium. An exemplary storage medium can be coupled to the processor such the processor can read information from, and write information to, the storage medium. In the alternative, the storage medium can be integral to the processor. The processor and the storage medium can also reside in an ASIC.

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein represent a presently preferred embodiment of the invention and are therefore representative of the subject matter which is broadly contemplated by the present invention. It is further understood that the scope of the present invention fully encompasses other embodiments that may become obvious to those skilled in the art and that the scope of the present invention is accordingly not limited.

The invention claimed is:

1. A sensor assembly for providing a polysomnography pillow for use by a user having a head and a heart, the sensor comprising:

at least one sensor configured to be coupled to a pillow body, wherein the at least one sensor comprises a tilt sensor that is configured to generate respiratory effort signals based on tilting of a head of a user on the pillow, wherein the at least one sensor is configured to generate ballistocardiogram signals from movement of the head of the user caused by beating of the heart of the user.

2. The sensor assembly of claim 1, wherein the at least one sensor is a tri-axial accelerometer.

3. The sensor assembly of claim 1, wherein the at least one sensor comprises at least two sensors.

4. The sensor assembly of claim 1, further comprising at least one secondary sensor configured to measure secondary patient information.

5. The sensor assembly of claim 4, wherein the at least one secondary sensor comprises at least one of an electromyography sensor, an electro-oculography sensor, a nasal pressure sensor, or an electroencephalography sensor.

6. The sensor assembly of claim 4, wherein the at least one secondary sensor comprises one or more pulse oximetry sensors.

7. The sensor assembly of claim 1, wherein the at least one sensor is configured to transmit sensed data to a data collection device.

8. The sensor assembly of claim 7, wherein the at least one sensor is configured to wirelessly transmit sensed data to the data collection device.

9. The sensor assembly of claim 1, wherein the at least one sensor is configured to store data associated with the respiratory effort signals.

10. A system comprising:
a sensor assembly for providing a polysomnography pillow for use by a user having a head and a heart, the sensor assembly comprising at least one sensor configured to be coupled to a pillow body, wherein the at least one sensor comprises a tilt sensor that is configured to generate respiratory effort signals based on tilting of a head of a user on the pillow body, wherein the at least one sensor is configured to generate ballistocardiogram signals from movement of the head of the user caused by beating of the heart of the user; and
a data collection device configured to communicate with the sensor assembly.

11. The system of claim 10, wherein the data collection device comprises a data storage area.

12. The system of claim 10, wherein the data collection device is configured to transmit data associated with the respiratory effort signals to a remote device.

13. The system of claim 12, wherein the data collection device is configured to transmit the data associated with the respiratory effort signals to the remote device via a cellular network.

14. The system of claim 10, wherein the at least one sensor comprises at least two sensors embedded in the pillow body.

15. The system of claim 10, further comprising at least one secondary sensor configured to measure secondary patient information.

16. The system of claim 15, wherein the at least one secondary sensor comprises at least one of an electromyography sensor, an electro-oculography sensor, a nasal pressure sensor, or an electroencephalography sensor.

17. The system of claim 15, wherein the at least one secondary sensor comprises one or more pulse oximetry sensors.

18. The system of claim 10, wherein the at least one sensor is configured to transmit sensed data to the data collection device.

19. The system of claim 18, wherein the at least one sensor is configured to wirelessly transmit sensed data to the data collection device.

20. The system of claim 10, wherein the at least one sensor is configured to store data associated with the respiratory effort signals.

* * * * *